(12) United States Patent
Alhajri et al.

(10) Patent No.: US 11,931,727 B2
(45) Date of Patent: Mar. 19, 2024

(54) NICKEL-IRON CATALYST AND METHODS OF MAKING AND USING SAME

(71) Applicant: Saudi Arabian Oil Company, Dhahran (SA)

(72) Inventors: Nawal Saad Alhajri, Dammam (SA); Mohammed A. Albuali, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/731,434

(22) Filed: Apr. 28, 2022

(65) Prior Publication Data

US 2023/0347321 A1 Nov. 2, 2023

(51) Int. Cl.
| | |
|---|---|
| *B01J 23/75* | (2006.01) |
| *B01J 21/16* | (2006.01) |
| *B01J 37/02* | (2006.01) |
| *C01B 3/26* | (2006.01) |
| *C01B 32/50* | (2017.01) |
| *C07C 1/04* | (2006.01) |

(52) U.S. Cl.
CPC ............ *B01J 23/75* (2013.01); *B01J 21/16* (2013.01); *B01J 37/0201* (2013.01); *C01B 3/26* (2013.01); *C01B 32/50* (2017.08); *C07C 1/044* (2013.01); *C01B 2203/0205* (2013.01); *C07C 2521/16* (2013.01); *C07C 2523/42* (2013.01); *C07C 2523/44* (2013.01)

(58) Field of Classification Search
CPC ... B01J 21/16; B01J 23/70; B01J 23/74; B01J 23/745; B01J 23/75; B01J 23/755; B01J 37/0201; C01B 3/26; C01B 23/50; C01B 2203/0205; C07C 1/044; C07C 2521/16; C07C 2523/42; C07C 2523/44
See application file for complete search history.

(56) References Cited

U.S. PATENT DOCUMENTS

| | | | |
|---|---|---|---|
| 5,066,629 | A | 11/1991 | Lukey et al. |
| 8,309,485 | B2 | 11/2012 | Yang et al. |
| 9,409,150 | B2 | 8/2016 | D'Souza et al. |
| 9,782,751 | B2 | 10/2017 | D'Souza et al. |
| 10,179,326 | B2 | 1/2019 | Basset et al. |
| 10,556,224 | B2 | 2/2020 | Han et al. |
| 10,676,547 | B2 | 6/2020 | Holtcamp et al. |

(Continued)

FOREIGN PATENT DOCUMENTS

| | | | | |
|---|---|---|---|---|
| CN | 114272927 A | * | 4/2022 | ............ B01J 23/755 |
| GB | 813214 | | 5/1959 | |

OTHER PUBLICATIONS

Machine translation of Guo et al, CN 114272927, published Apr. 5, 2022. (Year: 2022).*

(Continued)

*Primary Examiner* — Brian A McCaig
(74) *Attorney, Agent, or Firm* — Fish & Richardson P.C.

(57) ABSTRACT

A catalyst includes a derivative of an iron-containing clay which includes at least one member selected from the group consisting of a nickel-iron bimetallic structure according to XRD and a nickel-iron bimetallic oxide structure according to XRD. The catalyst can be used in various reactions, such as carbon dioxide methanation and dry reforming of methane and carbon dioxide to produce syngas.

20 Claims, 5 Drawing Sheets

(56) References Cited

U.S. PATENT DOCUMENTS

2010/0197956 A1 8/2010 Hagemeyer et al.

OTHER PUBLICATIONS

Akri, M. et al, 2016, "Novel nickel promoted illite clay based catalyst for autothermal dry reforming of methane," Fuel, vol. 178, pp. 139-147. <http://dx.doi.org/10.1016/j.fuel.2016.03.018> (Year: 2016).*
U.S. Appl. No. 17/731,418, Alhajri et al., filed Apr. 28, 2022.
Pavlova et al., "Syngas production by CO 2 reforming of methane using LnFeNi (Ru) O 3 perovskites as precursors of robust catalysts." Catalysis Science & Technology 2.10, 2012, 2099-2108, 10 pages.

* cited by examiner

NICKEL-IRON CATALYST AND METHODS OF MAKING AND USING SAME

FIELD

The disclosure relates to nickel-iron catalysts and methods of making and using such catalysts. In certain embodiments, the catalysts can be used to catalyze a carbon dioxide methanation reaction. In some embodiments, the catalysts can be used to catalyze dry reforming of methane and carbon dioxide to produce syngas.

BACKGROUND

In carbon dioxide methanation, carbon dioxide ($CO_2$) and hydrogen ($H_2$) are converted to methane ($CH_4$) and water ($H_2O$). Thus, carbon dioxide methanation can serve as a source of methane, which has significant commercial use in the chemical industry. In dry reforming of methane and carbon dioxide, methane and carbon dioxide are converted to syngas, which contains hydrogen and carbon monoxide (CO). Therefore, dry reforming of methane and carbon dioxide enables the consumption of two greenhouse gases to produce syngas, which is an important feedstock in the chemical industry.

SUMMARY

The disclosure relates to catalysts and related methods of making and using such catalysts. The catalysts can exhibit good efficiency when used to catalyze carbon dioxide methanation and/or dry reforming of methane and carbon dioxide to produce syngas. The catalysts can be relatively easy and inexpensive to make.

In general, the catalysts are derivatives of iron-containing clays, wherein the catalysts include a nickel-iron bimetallic structure according to X-ray diffraction (XRD) and/or a nickel-iron bimetallic oxide structure according to XRD. Iron-containing clays can have desirable physicochemical and textural properties making them suitable materials for catalytic applications, such as a comparatively high surface area. As a result, the catalysts can also have a relatively high surface area, which can result in enhanced catalytic performance. Further, the catalysts can exhibit comparatively high reactant conversions, high product yields and/or good selectivity for the desired products, such as when used in carbon dioxide methanation and/or dry reforming of methane and carbon dioxide to produce syngas. In addition, the catalysts can also exhibit relatively low yields for undesirable products, such as carbon monoxide in carbon dioxide methanation. Moreover, iron-containing clays are relatively low in cost and comparatively abundant resulting in inexpensive catalysts and catalysts that are relatively inexpensive to make.

The disclosure provides methods of making the catalysts. In some embodiments, the methods include treating an iron-containing clay with an acid to form an intermediate followed by impregnating the intermediate with nickel. The methods can also include certain steps of heating, neutralization and/or drying. The methods of making the catalysts can be relatively simple and inexpensive.

In certain embodiments, the catalysts can be used to catalyze carbon dioxide methanation. Optionally, the resulting methane can be used in natural gas or as a feedstock to produce downstream products. The catalysts can exhibit high carbon dioxide conversion, high methane yields and/or low carbon monoxide yields. In some embodiments, the catalysts have a carbon dioxide conversion of at least 50% at a temperature of 400° C., a pressure of 1.5 bar, and a total feed gas hourly space velocity (GHSV) of 1060 $h^{-1}$. In certain embodiments, the catalysts have a methane yield of at least 20% at a temperature of 400° C., a pressure of 1.5 bar, and a total feed GHSV of 1060 $h^{-1}$. In some embodiments, the catalyst has a yield of carbon monoxide at a temperature of 400° C., a pressure of 1.5 bar, and a total feed GHSV of 1060 $h^{-1}$ that is so low that it is undetectable. For example, in certain embodiments, the catalyst has a yield of carbon monoxide of less than 1% (e.g., less than 0.5%) at a temperature of 400° C., a pressure of 1.5 bar, and a total feed GHSV of 1060 $h^{-1}$.

In certain embodiments, the catalysts can be used to catalyze dry reforming of methane and carbon dioxide to produce syngas. In such reactions, greenhouse gases are converted to a useful feedstock for the production of various chemicals. The catalyst cans exhibit high carbon dioxide conversion, high methane conversion and/or high hydrogen yield. In certain embodiments, the catalyst has a carbon dioxide conversion of at least 80% at a temperature of 800° C., a pressure of 2 bar, and a total feed GHSV of 1477 $h^{-1}$. In certain embodiments, the catalyst has a methane conversion of at least 80% at a temperature of 800° C., a pressure of 2 bar, and a total feed GHSV of 1477 $h^{-1}$. In certain embodiments, the catalyst has a hydrogen yield of at least 50% at a temperature of 800° C., a pressure of 2 bar, and a gas hourly space velocity of 1477 $h^{-1}$.

In a first aspect, the disclosure provides a catalyst that includes a derivative of an iron-containing clay which includes at least one member selected from the group consisting of a nickel-iron bimetallic structure according to XRD and a nickel-iron bimetallic oxide structure according to XRD.

In some embodiments, according to XRD, the catalyst includes a nickel-iron bimetallic structure, such as $Fe_{0.5}Ni_{0.49}$, according to XRD.

In some embodiments, the catalyst includes a nickel-iron bimetallic oxide structure, such as $Fe_{1.7}Ni_{1.4}O_4$, according to XRD.

In some embodiments, the catalyst includes a nickel-iron bimetallic structure according to XRD and a nickel-iron bimetallic oxide structure according to XRD.

In some embodiments, the catalyst includes at least 10 weight percent nickel oxide according to X-ray fluorescence (XRF).

In some embodiments, according to XRF, the catalyst includes at least one oxide of a member selected from the group consisting of iron, silicon, aluminum and calcium.

In some embodiments, the iron-containing clay includes at least one member selected from the group consisting of nontronite, illite and actinolite.

In some embodiments, the catalyst has a surface area of at least 40 $m^2g^{-1}$.

In a second aspect, the disclosure provides a method that includes treating an iron-containing clay with an acid to form an intermediate, and impregnating the intermediate with nickel. The method forms a catalyst which includes a derivative of an iron-containing clay which includes at least one member selected from the group consisting of a nickel-iron bimetallic structure according to XRD and a nickel-iron bimetallic oxide structure according to XRD.

In some embodiments, the acid includes a member selected from the group consisting of hydrochloric acid and sulfuric acid.

In some embodiments, impregnating the intermediate with nickel includes contacting the intermediate with a nickel salt.

In some embodiments, treating the iron with the acid to form the intermediate includes heating to at least 50° C. for at least 30 minutes.

In some embodiments, treating the iron with the acid to form the intermediate includes neutralizing the acid.

In a third aspect, the disclosure provides a method that includes using a catalyst to convert carbon dioxide and hydrogen to methane and water. The catalyst includes a derivative of an iron-containing clay which includes at least one member selected from the group consisting of a nickel-iron bimetallic structure according to XRD and a nickel-iron bimetallic oxide structure according to XRD.

In some embodiments, the catalyst has a carbon dioxide conversion of at least 50% (e.g., at least 60%) at a temperature of 400° C., a pressure of 1.5 bar, and a total feed GHSV of 1060 $h^{-1}$.

In some embodiments, the catalyst has a yield of methane of at least 20% (e.g., at least 25%) at a temperature of 400° C., a pressure of 1.5 bar, and a total feed GHSV of 1060 $h^{-1}$.

In some embodiments, the catalyst has a yield of carbon monoxide at a temperature of 400° C., a pressure of 1.5 bar, and a total feed GHSV of 1060 $h^{-1}$ that is so low that it is undetectable. For example in certain embodiments, the catalyst has a yield of carbon monoxide of less than 1% (e.g., less than 0.5%) at a temperature of 400° C., a pressure of 1.5 bar, and a total feed GHSV of 1060 $h^{-1}$.

In some embodiments, according to XRF, the catalyst includes at least one oxide of a member selected from the group consisting of nickel, iron, silicon, aluminum and calcium. And the iron-containing clay includes at least one member selected from the group consisting of nontronite, illite and actinolite.

In a fourth aspect, the disclosure provides a method that includes using a catalyst to convert methane and carbon dioxide to hydrogen and carbon monoxide. The catalyst includes a derivative of an iron-containing clay which includes at least one member selected from the group consisting of a nickel-iron bimetallic structure according to XRD and a nickel-iron bimetallic oxide structure according to XRD.

In some embodiments, the catalyst has a carbon dioxide conversion of at least 80% (e.g., at least 85%) at a temperature of 800° C., a pressure of 2 bar, and a total feed GHSV of 1477 $h^{-1}$.

In some embodiments, the catalyst has a methane conversion of at least 80% (e.g., at least 85%) at a temperature of 800° C., a pressure of 2 bar, and a total feed GHSV of 1477 $h^{-1}$.

In some embodiments, the catalyst has a yield of hydrogen gas of at least 50% (e.g., at least 60%) at a temperature of 800° C., a pressure of 2 bar, and a total feed GHSV of 1477 $h^{-1}$.

In some embodiments, the catalyst includes a nickel-iron bimetallic structure, such as $Fe_{0.5}Ni_{0.49}$, according to XRD.

In some embodiments, the catalyst includes a nickel-iron bimetallic oxide structure, such as $Fe_{1.7}Ni_{1.4}O_4$, according to XRD.

In some embodiments, the catalyst includes a nickel-iron bimetallic structure according to XRD and a nickel-iron bimetallic oxide structure according to XRD.

In some embodiments, the catalyst includes at least 10 weight percent nickel oxide according to XRF.

In some embodiments, according to XRF, the catalyst includes at least one oxide of a member selected from the group consisting of iron, silicon, aluminum and calcium.

In some embodiments, the iron-containing clay includes at least one member selected from the group consisting of nontronite, illite and actinolite.

In some embodiments, the catalyst has a surface area of at least 40 $m^2g^{-1}$.

In some embodiments, the method further includes treating the iron-containing clay with an acid to form an intermediate, impregnating the intermediate with nickel. In some embodiments, the acid is hydrochloric acid or sulfuric acid. In some embodiments, impregnating the intermediate with nickel includes contacting the intermediate with a nickel salt. In some embodiments, treating the iron with the acid to form the intermediate includes heating to at least 50° C. for at least 30 minutes. In some embodiments, treating the iron with the acid to form the intermediate includes neutralizing the acid.

DETAILED DESCRIPTION

Catalysts

Figure 1:
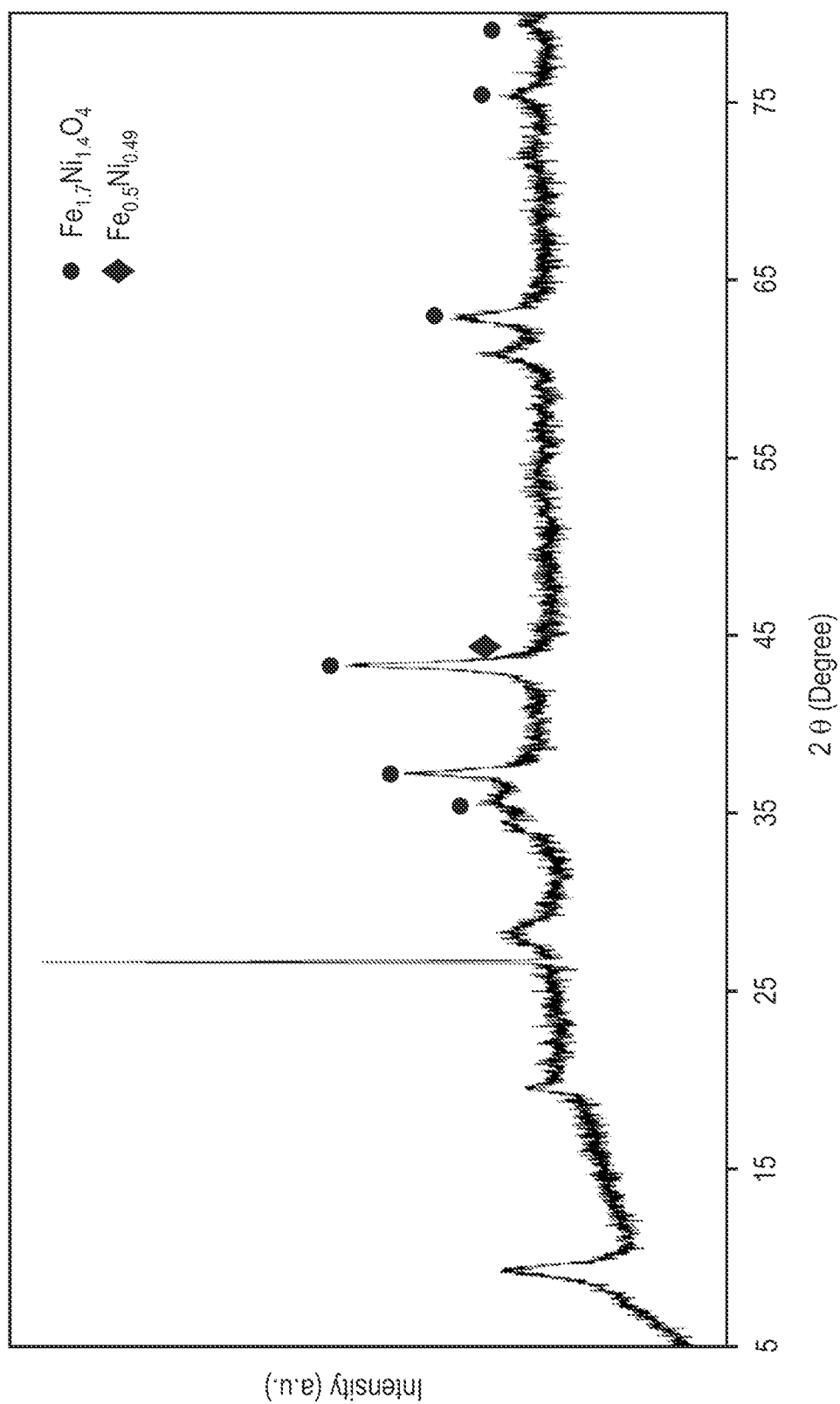
FIG. 1 is an XRD pattern of a catalyst.

Generally, a catalyst according to the disclosure is a derivative of an iron-containing clay, wherein the catalyst includes a nickel-iron bimetallic structure according to XRD and/or a nickel-iron bimetallic oxide structure according to XRD.

In some embodiments, the iron-containing clay is a smectite clay, such as nontronite. In certain embodiments, the iron-containing clay is illite or actinolite. In some embodiments, the iron-containing clay is a locally available clay. Without wishing to be bound by theory, it is believed that the nickel-iron bimetallic structure and/or the nickel-iron bimetallic oxide structure is an active catalyst for $CO_2$ methanation and/or for dry reforming reaction. Also without wishing to be bound by theory, it is believed that the iron-containing clay serves as an iron source for the active phase of the catalyst. Further without wishing to be bound by theory, it is believed that the physicochemical and textural properties, such as the aluminosilicate phase and porous structure, of the iron-containing clay allow it to serve as a good catalyst support as well as a promoter catalyst for $CO_2$ methanation and/or for dry reforming reaction. The modified iron-containing clay serves as the active and support catalyst for $CO_2$ methanation and/or for dry reforming reaction.

The nickel-iron bimetallic structure according to XRD results from an interaction between nickel and iron in the catalyst. In some embodiments, according to XRD, the nickel-iron bimetallic is $Fe_{0.5}Ni_{0.49}$.

In certain embodiments, according to XRD, the nickel-iron bimetallic oxide is $Fe_{1.7}Ni_{1.4}O_4$.

In general, according to XRF, the catalyst further includes oxides of nickel, iron, aluminum, silicon and/or calcium. In some embodiments, according to XRF, the catalyst includes nickel oxide (NiO), iron oxide ($Fe_2O_3$), silicon dioxide ($SiO_2$), aluminum oxide ($Al_2O_3$), and/or calcium oxide (CaO). Typically, according to XRF, each of these oxides is present in the catalyst. Generally, the concentration of NiO in the catalyst depends on the Ni loading during the synthesis of the catalyst. Often, the concentration of each of the oxides of iron, silicon, aluminum and calcium is determined by the concentration of the oxide in the iron-containing clay.

In certain embodiments, according to XRF, the catalyst contains 10-65 weight percent (wt. %) (e.g., 10-55 wt. %, 20-65 wt. %, 20-55 wt. %, 25-65 wt. %, 25-55 wt., 30-65 wt. %, 30-55 wt. %, 35-65 wt. %, 35-55 wt., 40-65 wt. %, 40-55 wt. %, 45-65 wt. %, 45-55 wt. %, 50-55 wt. %) NiO.

In some embodiments, according to XRF, the catalyst contains 10-60 wt. % (e.g., 10-50 wt. %, 20-60 wt. %, 20-50 wt. %, 30-60 wt. %, 30-50 wt. %, 40-65 wt. %, 40-50 wt. %, 40-45 wt. %) $Fe_2O_3$.

In certain embodiments, according to XRF, the catalyst contains 1-10 wt. % (e.g., 1-8 wt. %, 1-6 wt. %, 2-10 wt. %, 2-8 wt. %, 2-6 wt. %, 3-10 wt. %, 3-8 wt. %, 3-6 wt. %) $SiO_2$.

In some embodiments, according to XRF, the catalyst contains 0.1-2 wt. % (e.g., 0.1-1.5 wt. %, 0.2-2 wt. %, 0.2-1.5 wt. %, 0.5-2 wt. %, 0.5-1.5 wt. %, 1-2 wt. %, 1-1.5 wt. %) $Al_2O_3$.

In certain embodiments, according to XRF, the catalyst contains 0.1-1 wt. % (e.g., 0.1-0.8 wt. %, 0.2-1 wt. %, 0.2-0.8 wt. %, 0.4-1 wt. %, 0.4-0.8 wt. %) CaO.

In certain embodiments, according to XRF, the catalyst contains: a) 10-65 wt. % (e.g., 10-55 wt. %, 20-65 wt. %, 20-55 wt. %, 25-65 wt. %, 25-55 wt., 30-65 wt. %, 30-55 wt. %, 35-65 wt. %, 35-55 wt., 40-65 wt. %, 40-55 wt. %, 45-65 wt. %, 45-55 wt. %, 50-55 wt. %) NiO; b) 10-60 wt. % (e.g., 10-50 wt. %, 20-60 wt. %, 20-50 wt. %, 30-60 wt. %, 30-50 wt. %, 40-65 wt. %, 40-50 wt. %, 40-45 wt. %) $Fe_2O_3$; c) the catalyst contains 1-10 wt. % (e.g., 1-8 wt. %, 1-6 wt. %, 2-10 wt. %, 2-8 wt. %, 2-6 wt. %, 3-10 wt. %, 3-8 wt. %, 3-6 wt. %) $SiO_2$; d) 0.1-2 wt. % (e.g., 0.1-1.5 wt. %, 0.2-2 wt. %, 0.2-1.5 wt. %, 0.5-2 wt. %, 0.5-1.5 wt. %, 1-2 wt. %, 1-1.5 wt. %) $Al_2O_3$; and e) 0.1-1 wt. % (e.g., 0.1-0.8 wt. %, 0.2-1 wt. %, 0.2-0.8 wt. %, 0.4-1 wt. %, 0.4-0.8 wt. %) CaO.

In some embodiments, the catalyst may have at least one XRD peak (e.g. a least two XRD peaks, at least three XRD peaks, at least four XRD peaks, at least five XRD peaks, at least six XRD peaks, at least seven XRD peaks) as depicted in FIG. 1. In some embodiments, the catalyst may have an XRD pattern as substantially depicted in FIG. 1.

In certain embodiments, the catalyst has textural properties distinct from those of the iron-containing clay starting material that are beneficial for catalysis. As an example, in certain embodiments, the catalyst has a surface area greater than the surface area of the iron-containing clay starting material. In certain embodiments, the catalyst has a surface area of at least 40 $m^2g^{-1}$ (e.g. at least 50 $m^2g^{-1}$, 60 $m^2g^{-1}$, 70 $m^2g^{-1}$, 80 $m^2g^{-1}$, 90 $m^2g^{-1}$) and/or at most 250 $m^2g^{-1}$ (e.g., at most 200 $m^2g^{-1}$). In certain embodiments, the surface area is determined by $N_2$ sorption.

Methods of Making Catalysts

In general, the catalyst is made by a method that includes first modifying the iron-containing clay, followed by incorporation (impregnation) of nickel. In certain embodiments, the iron-containing clay is modified by acid treatment.

In some embodiments, the method includes treating the iron-containing clay with an acid, such as hydrochloric acid or sulfuric acid, to form an intermediate. As an example, a mixture containing the iron-containing clay and acid can be heated to at least 50° C. (e.g., at least 60° C., at least 70° C., at least 80° C., at least 90° C.) and/or at most 100° C. for at least 30 minutes (e.g. at least one hour, at least two hours, at least three hours, at least four hours) and/or at most five hours.

In certain embodiments, the resulting liquid is neutralized with a base, such as ammonium hydroxide, to attain a pH of 6.5-7.5 (e.g., 7). Optionally, this step can be performed by slowly adding the base while stirring.

In some embodiments, the resulting liquid is filtered and dried at an elevated temperature (e.g., at 90-110° C., such as at 100° C.) for a period of time (e.g., 5 hours to 24 hours) to produce an intermediate (acid activated iron-containing clay).

In some embodiments, a nickel salt, such as nickel nitrate hexahydrate or nickel chloride, is dissolved in a solvent, such as ethanol, and the resulting solution and intermediate are mixed with stirring for a period of time (e.g., 3-5 hours, such as 4 hours) to produce a sample.

In certain embodiments, the sample is dried at an elevated temperature (e.g., at 90-110° C., such as at 100° C.) for a period of time (e.g., 4-6 hours) followed by calcination at an elevated temperature (e.g., 400-800° C., 500-700° C., 600° C.) for a period of time (e.g., 2-4 hours, such as 3 hours) to yield the catalyst.

Methods of Using Catalysts for Carbon Dioxide Methanation

In some embodiments, the catalyst is used to catalyze carbon dioxide methanation in which carbon dioxide and hydrogen are converted to methane and water. In such embodiments, the catalyst can exhibit a high carbon dioxide conversion, a high methane yield and/or a low carbon monoxide yields. In certain embodiments, the catalyst can have a carbon dioxide conversion of 50-99% (e.g., 50-95%, 60-99%, 60-95%, 70-99%, 70-95%, 80-99%, 80-95%) at a temperature of 400° C., a pressure of 1.5 bar, and a total feed GHSV of 1060 $h^{-1}$. In some embodiments, the catalysts can have a methane yield of 20-50% (e.g., 20-45%, 20-40%, 25-50%, 25-45%, 25-40%, 30-45%, 30-40%) at a temperature of 400° C., a pressure of 1.5 bar, and a total feed GHSV of 1060 $h^{-1}$. In certain embodiments, the catalyst can have a carbon monoxide yield of less than 40% (e.g., less than 35%, less than 30%, less than 20%, less than 10%, less than 9%, less than 8%, less than 7%, less than 6%, less than 5%, less than 4%, less than 3%, less than 2%, less than 1%, less than 0.5%, less than 0.1%) at a temperature of 400° C., a pressure of 1.5 bar, and a total feed GHSV of 1060 $h^{-1}$. In some embodiments, the catalyst can have a carbon monoxide yield that is below the detection limit of the instrument used to determine the yield.

In some embodiments, the methane produced is used as natural gas, e.g., in a commercial and/or industrial setting. In some embodiments, the methane produced is used as a feedstock to produce downstream products, such as ethylene, hydrogen and/or ammonia.

Methods of Using Catalysts for Dry Reforming

In certain embodiments, the catalysts are used to catalyze dry reforming of methane and carbon dioxide to produce syngas, which includes hydrogen and carbon monoxide. In such embodiments, the catalyst can exhibit a high carbon dioxide conversion, a high methane conversion and/or a high hydrogen yield. In certain embodiments, the catalyst can have a carbon dioxide conversion of 60-99% (e.g., 60-95%, 60-90%, 70-99%, 70-95%, 70-90%, 75-99%, 75-95%, 75-90%, 80-99%, 80-95%, 80-90%) at a temperature of 800° C., a pressure of 2 bar, and a total feed GHSV of 1477 $h^{-1}$. In some embodiments, the catalyst can have a methane conversion of 60-95% (e.g., 60-90%, 70-95%, 70-90%, 75-95%, 75-90%, 80-95%, 80-90%) at a temperature of 800° C., a pressure of 2 bar, and a total feed GHSV of 1477 h$^{-1}$. In certain embodiments, the catalyst can have a hydrogen yield of 40-95% (e.g. 40-90%, 40-80%, 40-70%, 40-60%, 50-95%, 50-90%, 50-80%, 50-70%, 50-60%, 75-95%, 75-90%, 80-95%, 80-90%) at a temperature of 800° C., a pressure of 2 bar, and a gas hourly space velocity of 1477 h$^{-1}$.

In certain embodiments, the syngas generated has a desirable H$_2$/CO ratio for Fischer-Tropsch synthesis of liquid hydrocarbons and/or the synthesis of oxygenated chemical compounds.

EXAMPLES

Example 1: Synthesis of Catalyst grams of nontronite (Cheney, Washington, Ward's Natural Science Establishment, Inc., having a surface area of 29 m$^2$ g$^{-1}$ as determined by N$_2$ sorption) was dissolved in 100 milliliters of deionized water. 33 milliliters of 37% hydrochloric acid (Sigma-Aldrich) were mixed with 367 milliliters of deionized water and added to the nontronite solution. The mixture was stirred and heated at 60° C. for 4 hours. 30 milliliters of ammonium hydroxide (Sigma-Aldrich) was slowly added to the mixture while stirring until a pH of 7 was reached. The resulting solution was filtered and dried in the oven at 100° C. to produce acid activated nontronite clay. 12 grams of nickel nitrate hexahydrate (Sigma-Aldrich) were dissolved in 50 milliliters of ethanol (Sigma-Aldrich), and the resulting solution was mixed with the acid activated nontronite clay and stirred for 4 hours. The produced sample was dried in the oven at 100° C. followed by calcination at 600° C. for 3 hours.

The catalyst had a surface area of 91 m$^2$ g$^{-1}$ as determined by N$_2$ sorption. 0.7 g of catalyst in the form of a powder was pressed with 0.9 g XRF binder (CEREOX® wax binder, FLUXANA) to provide a sample for XRF. Table 1 shows information regarding constituents of the catalyst in the sample as determined using XRF. The remainder of the sample (to equal 100%) was taken up by the binder (hydrogen and carbon). Table 2 shows information regarding constituents of the catalyst, correcting for the presence of the binder.

TABLE 1

| Oxides | NiO | Fe$_2$O$_3$ | SiO$_2$ | Al$_2$O$_3$ | CaO |
|---|---|---|---|---|---|
| Concentration (wt %) | 20.8 | 16.2 | 1.7 | 0.3 | 0.2 |

TABLE 2

| Oxides | NiO | Fe$_2$O$_3$ | SiO$_2$ | Al$_2$O$_3$ | CaO |
|---|---|---|---|---|---|
| Concentration (wt %) | 48.5 | 43.4 | 5.5 | 1.1 | 0.5 |

FIG. 1 is an XRD pattern of the catalyst in Example 1. The XRD pattern shows that the catalyst contained a nickel-iron bimetallic structure (Fe$_{0.5}$Ni$_{0.49}$) in which there was an interaction between iron and nickel. The XRD pattern also shows that the catalyst contained a nickel-iron bimetallic oxide structure (Fe$_{1.7}$Ni$_{1.4}$O$_4$).

Example 2: Carbon Dioxide Methanation

Catalyst prepared according to Example 1 was used in a carbon dioxide methanation experiment at temperatures of 300° C. and 400° C. and a pressure of 1.5 bar. A feed gas containing 25% carbon dioxide and 75% hydrogen flowed over the catalyst at a total feed GHSV of 1060 h$^{-1}$. The experiment was performed using a PID reactor system (PID ENG&TECH).

The CO$_2$ conversion was calculated as:

$$CO_2 \text{ conversion } (\%) = \frac{\text{Moles of } CO_2 \text{ consumed}}{\text{Moles of } CO_2 \text{ provided}} \times 100.$$

The methane yield (%) was calculated as:

$$\text{Methane yield } (\%) = \frac{\text{Actual yield}}{\text{Theoretical yield}} \times 100.$$

Figure 2:
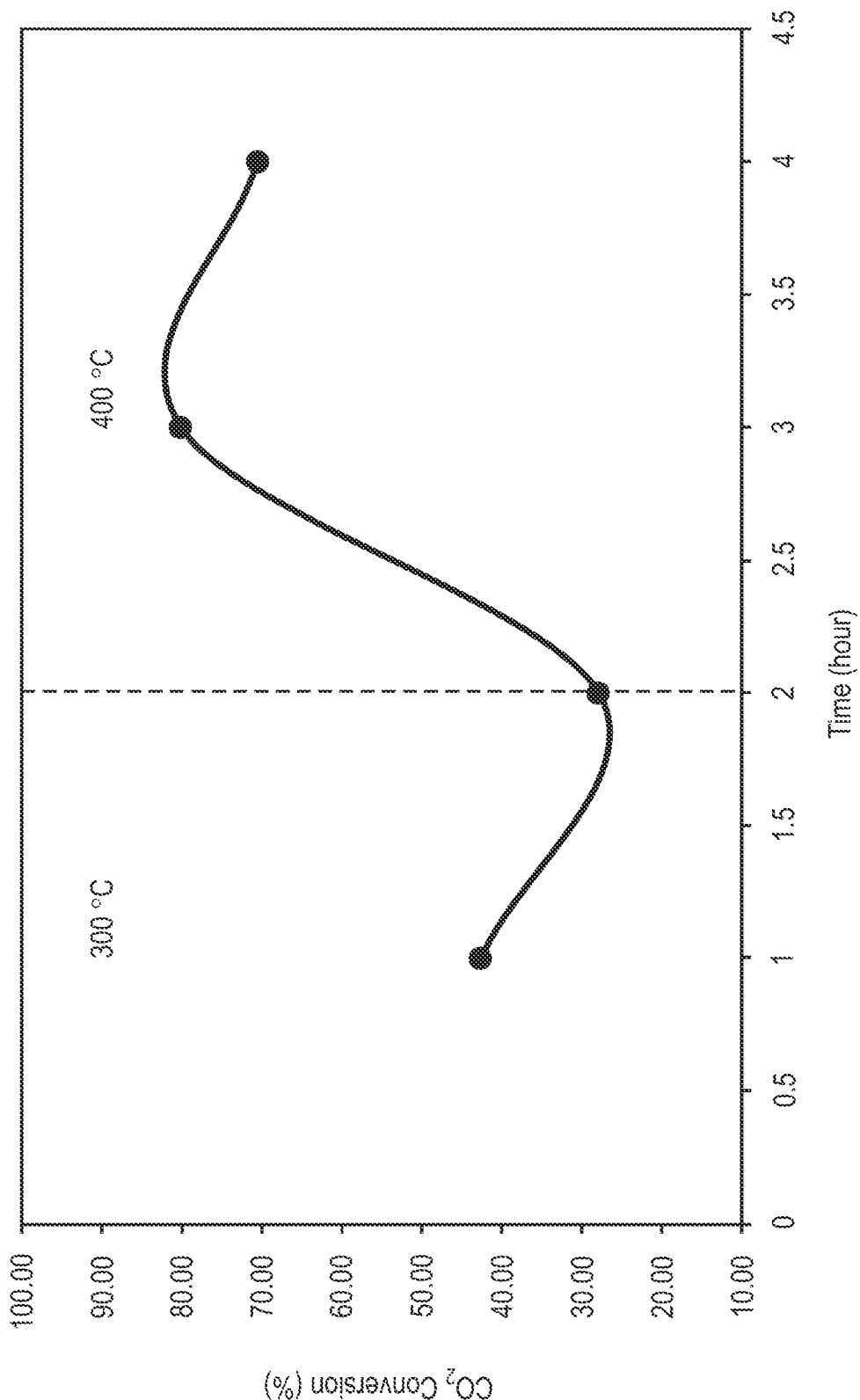
FIG. 2 shows a graph of $CO_2$ conversion data during catalyzed carbon dioxide methanation.

The measured CO$_2$ conversion (%) is shown in FIG. 2. The methane yield (%) was measured using gas chromatography and is shown in FIG. 3.

Figure 3:
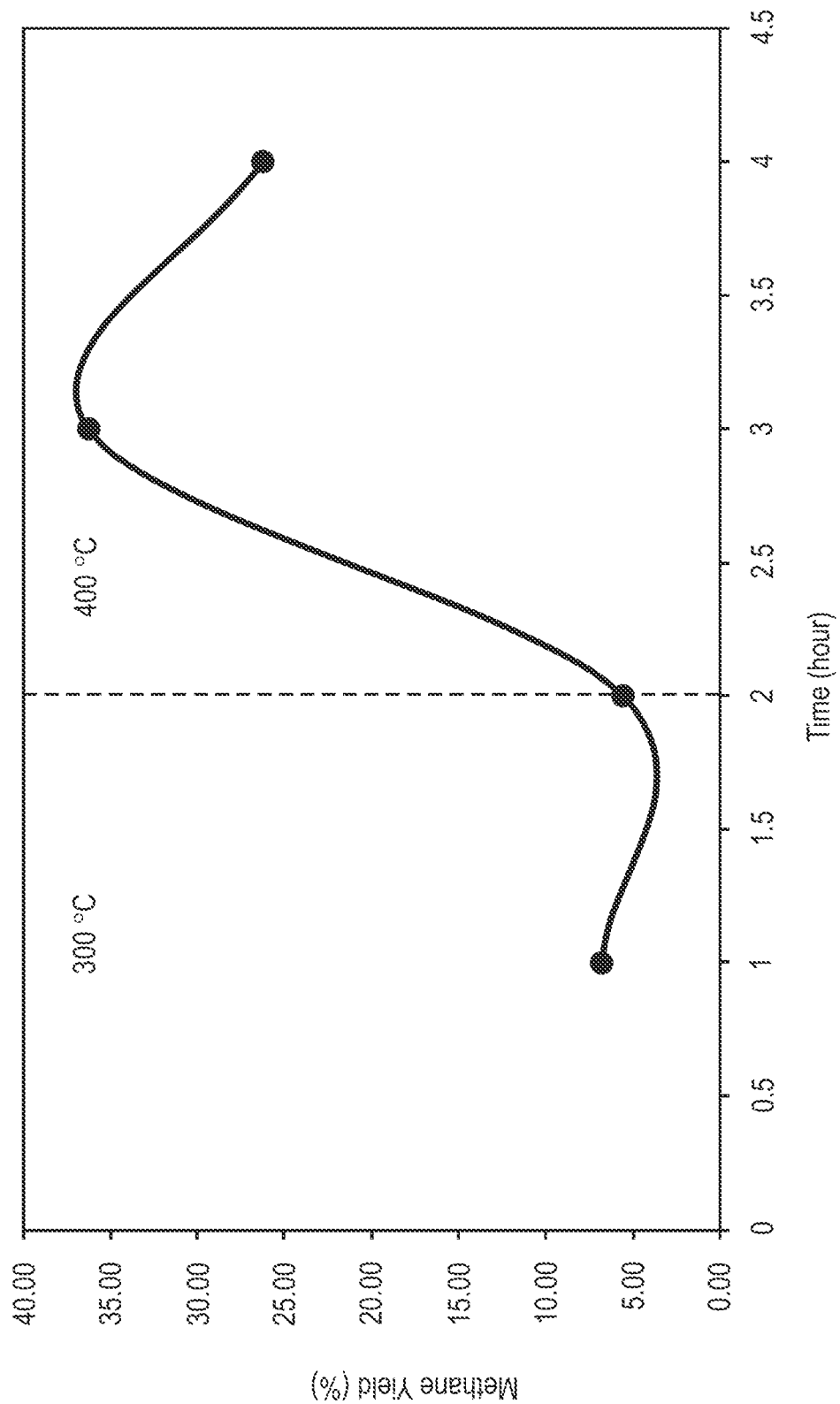
FIG. 3 shows a graph of methane yield during catalyzed carbon dioxide methanation.

As shown in FIGS. 2 and 3, the carbon dioxide methanation experiment showed that the catalyst provided good CO$_2$ conversion and good methane yield.

Example 3: Dry Reforming of Methane

Catalyst prepared according to Example 1 was used in a dry reforming of methane experiment at a temperature of 800° C., a pressure of 2 bar. A feed gas containing carbon dioxide and methane at a total feed GHSV 1477 h$^{-1}$. The experiment was performed using a PID reactor system (PID ENG&TECH).

The methane conversion was calculated as:

$$\text{Methane conversion } (\%) = \frac{\text{Moles of methane consumed}}{\text{Moles of methane provided}} \times 100.$$

The hydrogen gas yield (%) was calculated as:

$$\text{Hydrogen yield } (\%) = \frac{\text{Actual yield}}{\text{Theoretical yield}} \times 100.$$

The CO$_2$ conversion was calculated as:

$$CO_2 \text{ conversion } (\%) = \frac{\text{Moles of } CO_2 \text{ consumed}}{\text{Moles of } CO_2 \text{ provided}} \times 100.$$

Figure 4:
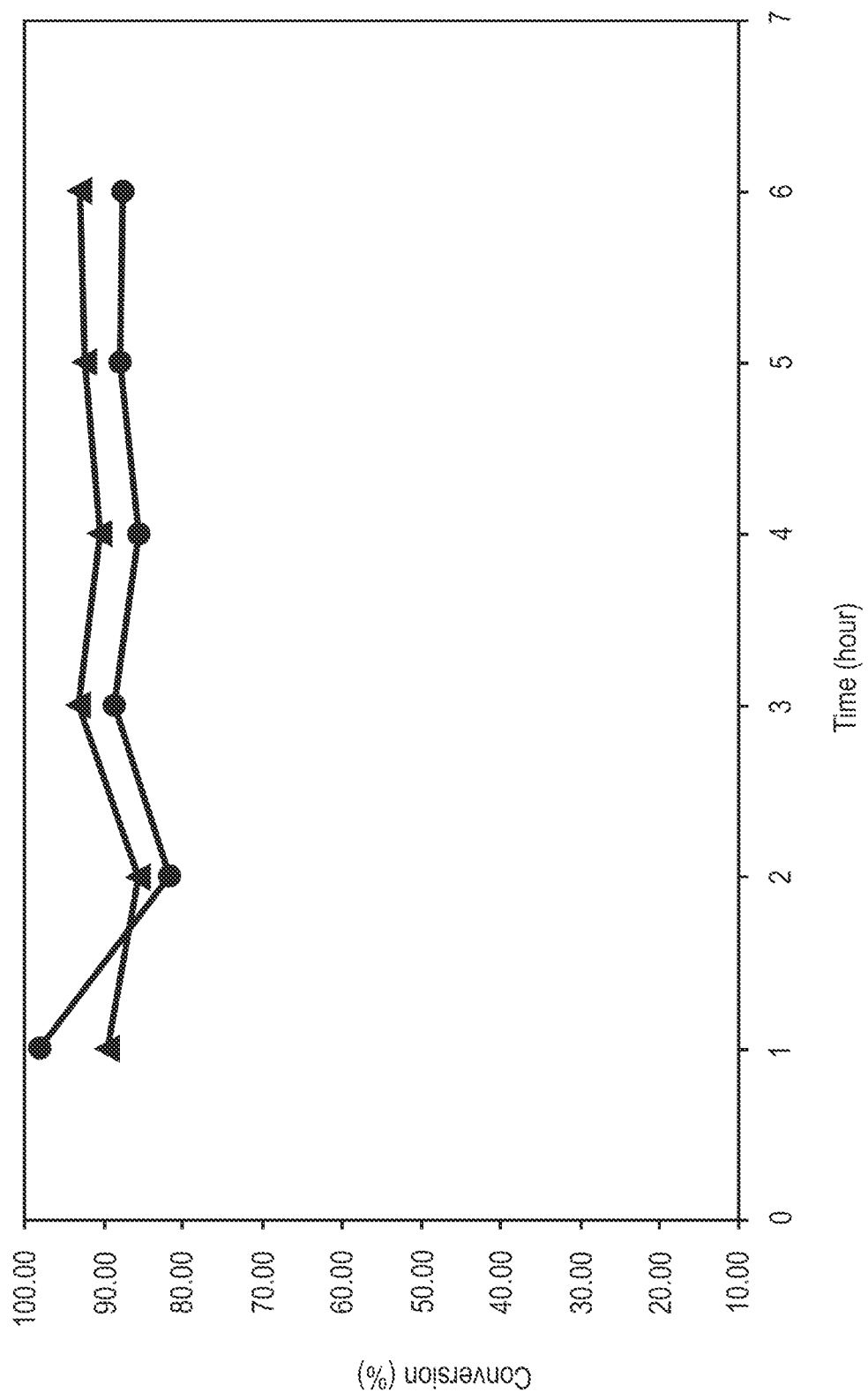
FIG. 4 shows graphs of $CO_2$ conversion and methane conversion during catalyzed dry reforming of methane and $CO_2$.
Figure 5:
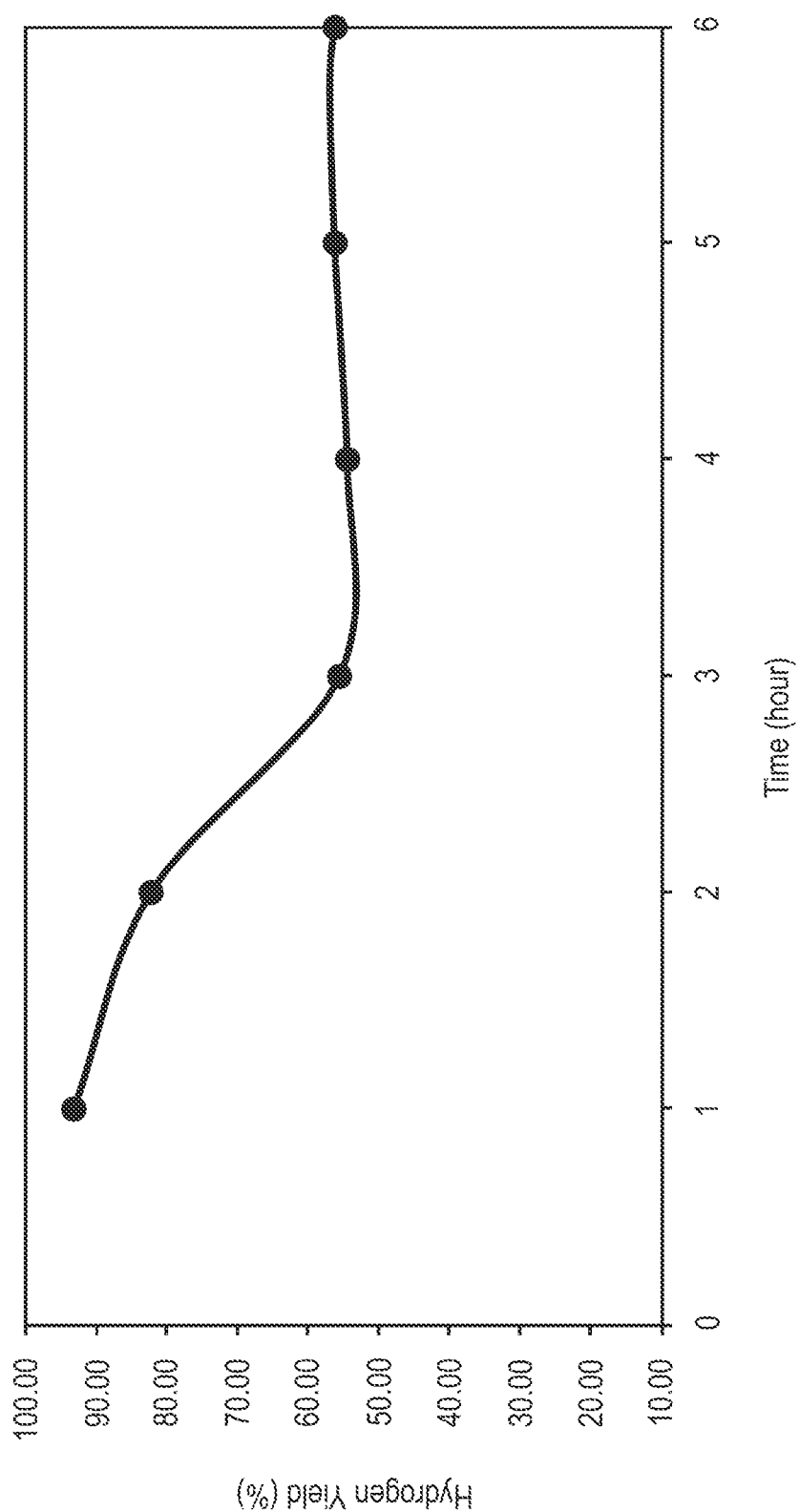
FIG. 5 shows a graph of hydrogen yield during catalyzed dry reforming of methane and $CO_2$.

The methane conversion (%) and the measured CO$_2$ conversion (%) were measured using gas chromatography and are shown in FIG. 4, where the triangles represent measured methane conversion (%) and the circles represent measured CO$_2$ conversion (%). The hydrogen yield (%) was measured using gas chromatography and is shown in FIG. 5. The carbon monoxide yield (%) was measured using gas chromatography and was about 35%.

As shown in FIGS. 4 and 5, the dry reforming of methane experiment showed that the catalyst provided good CO$_2$ conversion, good methane conversion and good hydrogen yield. A relatively low carbon monoxide yield was also obtained.

Other Embodiments

While certain embodiments have been described, the disclosure is not limited to such embodiments.

As an example, while the catalysts have been described as being used in dry reforming of methane and carbon dioxide to produce syngas, the disclosure is not limited in this manner. For example, in some embodiments, the catalysts can be used in dry reforming of other alkanes (e.g., ethane, propane) to form syngas.

As another example, while certain methods of using the catalysts have been described, the disclosure is not limited to such uses. For example, in some embodiments, the catalysts can be used to catalyze the hydrogenation of $CO_2$ to form products other than methane, such as one or more alcohols and/or one or more olefins. Further examples include hydrogenation reactions, reforming of hydrocarbons, dehydrogenation of ammonia, and conversion of $CO_x$ to hydrocarbons.

What is claimed is:

1. A catalyst, comprising:
a derivative of an iron-containing clay which comprises at least one member selected from the group consisting of a nickel-iron bimetallic structure according to X-ray diffraction and a nickel-iron bimetallic oxide structure according to X-ray diffraction,
wherein the catalyst has a surface area of at least 40 $m^2g^{-1}$, and
wherein the catalyst comprises at least 10 weight percent nickel oxide according to X-ray fluorescence.

2. The catalyst of claim 1, wherein the catalyst comprises a nickel-iron bimetallic structure according to X-ray diffraction.

3. The catalyst of claim 2, wherein the nickel-iron bimetallic structure comprises $Fe_{0.5}Ni_{0.49}$ according to X-ray diffraction.

4. The catalyst of claim 1, wherein the catalyst comprises a nickel-iron bimetallic oxide structure according to X-ray diffraction.

5. The catalyst of claim 4, wherein the nickel-iron bimetallic oxide structure comprises $Fe_{1.7}Ni_{1.4}O_4$ according to X-ray diffraction.

6. The catalyst of claim 1, wherein the catalyst comprises a nickel-iron bimetallic structure according to X-ray diffraction and a nickel-iron bimetallic oxide structure according to X-ray diffraction.

7. The catalyst of claim 1, wherein, according to X-ray fluorescence, the catalyst comprises at least one oxide of a member selected from the group consisting of iron, silicon, aluminum and calcium.

8. The catalyst of claim 1, wherein the iron-containing clay comprises at least one member selected from the group consisting of nontronite, illite and actinolite.

9. The catalyst of claim 1, wherein the catalyst has a surface area of at most 250 $m^2g^{-1}$.

10. A method, comprising:
contacting carbon dioxide and hydrogen with a catalyst to convert the carbon dioxide and hydrogen to methane and water,
wherein the catalyst comprises a derivative of an iron-containing clay which comprises at least one member selected from the group consisting of a nickel-iron bimetallic structure according to X-ray diffraction and a nickel-iron bimetallic oxide structure according to X-ray diffraction.

11. The method of claim 10, wherein the catalyst has a carbon dioxide conversion of at least 50% at a temperature of 400° C., a pressure of 1.5 bar, and a total feed gas hourly space velocity of 1060 $h^{-1}$.

12. The method of claim 10, wherein the catalyst has a yield of methane of at least 20% at a temperature of 400° C., a pressure of 1.5 bar, and a total feed gas hourly space velocity of 1060 $h^{-1}$.

13. The method of claim 10, wherein the catalyst has a yield of carbon monoxide of less than 1% at a temperature of 400° C., a pressure of 1.5 bar, and a total feed gas hourly space velocity of 1060 $h^{-1}$.

14. The method of claim 10, wherein:
according to X-ray fluorescence, the catalyst comprises at least one oxide of a member selected from the group consisting of nickel, iron, silicon, aluminum and calcium; and
the iron-containing clay comprises at least one member selected from the group consisting of nontronite, illite and actinolite.

15. The method of claim 10, wherein the catalyst has a surface area of at least 40 $m^2g^{-1}$.

16. The method of claim 10, wherein the catalyst has a surface area of at most 250 $m^2g^{-1}$.

17. The method of claim 10, wherein the catalyst comprises at least 10 weight percent nickel oxide according to X-ray fluorescence.

18. The method of claim 10, wherein the catalyst comprises a nickel-iron bimetallic structure according to X-ray diffraction.

19. The method of claim 18, wherein the catalyst comprises the nickel-iron bimetallic oxide structure according to X-ray diffraction.

20. The method of claim 10, wherein the catalyst comprises a nickel-iron bimetallic structure according to X-ray diffraction and a nickel-iron bimetallic oxide structure according to X-ray diffraction.

* * * * *